United States Patent
Antar et al.

(10) Patent No.: US 11,510,604 B2
(45) Date of Patent: Nov. 29, 2022

(54) SURFACE ELECTRODE FOR ACQUIRING A CARDIAC ACTIVITY OF A COATED ANIMAL, ELECTRODE SUPPORT, STRAP, ASSOCIATED METHODS

(71) Applicant: SEAVER, Paris (FR)

(72) Inventors: Zakaria Antar, Paris (FR); Pierre-Yves Lalo, Paris (FR)

(73) Assignee: SEAVER, Paris (FR)

( * ) Notice: Subject to any disclaimer, the term of this patent is extended or adjusted under 35 U.S.C. 154(b) by 326 days.

(21) Appl. No.: 16/629,209

(22) PCT Filed: Jul. 11, 2018

(86) PCT No.: PCT/EP2018/068812
§ 371 (c)(1),
(2) Date: Jan. 7, 2020

(87) PCT Pub. No.: WO2190/011994
PCT Pub. Date: Jan. 17, 2019

(65) Prior Publication Data
US 2020/0196901 A1    Jun. 25, 2020

(30) Foreign Application Priority Data
Jul. 12, 2017 (FR) ...................................... 1700747

(51) Int. Cl.
*A61B 5/282* (2021.01)
*A61B 5/0205* (2006.01)
(Continued)

(52) U.S. Cl.
CPC ............ *A61B 5/282* (2021.01); *A61B 5/0205* (2013.01); *A61B 5/1038* (2013.01);
(Continued)

(58) Field of Classification Search
CPC ..... A61B 5/282; A61B 5/0205; A61B 5/1038; A61B 5/6823; A61B 5/7278; A61B 5/743; A61B 2503/40; A61B 2562/0209
(Continued)

(56) References Cited

U.S. PATENT DOCUMENTS

| 4,540,001 A | 9/1985 | Ewing |
| 2004/0260166 A1 | 12/2004 | Merilainen |

(Continued)

FOREIGN PATENT DOCUMENTS

| FR | 3 041 233 A1 | 3/2017 |
| GB | 2 434 517 A | 8/2007 |
| JP | 3905358 B2 | 4/2007 |

OTHER PUBLICATIONS

International Search Report as issued in International Patent Application No. PCT/EP2018/068812, dated Nov. 23, 2018.
(Continued)

*Primary Examiner* — Carl H Layno
*Assistant Examiner* — Michael J Lau
(74) *Attorney, Agent, or Firm* — Pillsbury Winthrop Shaw Pittman LLP

(57) ABSTRACT

An electrode support includes a first reference electrode and a second electrode, the electrodes being electrically insulated from each other and able to measure two electric potentials at the surface of a haired animal body, the electrode support further including an electronic module including at least one memory, a calculator and a first electric interface to receive electric signals acquired from each electrode for recording a cardiac activity of the haired animal, the electrodes each including a one-piece structure formed of a polymer material in which conductive elements are distributed, the structure including a base and a plurality of projections able to go through a coat.

13 Claims, 4 Drawing Sheets

(51) Int. Cl.
*A61B 5/103* (2006.01)
*A61B 5/00* (2006.01)

(52) U.S. Cl.
CPC .......... *A61B 5/6823* (2013.01); *A61B 5/7278* (2013.01); *A61B 5/743* (2013.01); *A61B 2503/40* (2013.01); *A61B 2562/0209* (2013.01)

(58) Field of Classification Search
USPC ........................................................ 600/301
See application file for complete search history.

(56) References Cited

U.S. PATENT DOCUMENTS

| | | | |
|---|---|---|---|
| 2006/0106289 A1* | 5/2006 | Elser | A61B 5/389 600/300 |
| 2015/0238100 A1* | 8/2015 | Lin | A61B 5/398 600/393 |
| 2016/0089045 A1* | 3/2016 | Sadeghian-Motahar | A61B 5/0531 600/386 |
| 2016/0157718 A1* | 6/2016 | Barnes | G16H 20/30 600/509 |
| 2016/0296170 A1* | 10/2016 | Putila | A61B 5/0245 |

OTHER PUBLICATIONS

Notification Under Article 94(3) CBE as issued in European Patent Application No. 18740788.7, dated Jan. 13, 2021.
Notification Under Article 94(3) CBE as issued in European Patent Application No. 18740788.7, dated Jul. 13, 2020.

* cited by examiner

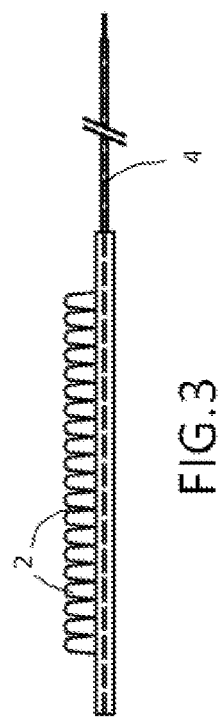
FIG.2
FIG.3
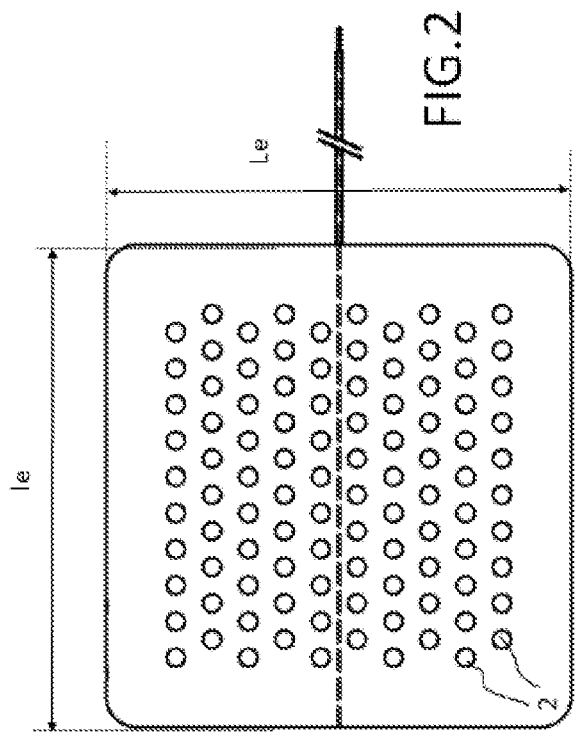
FIG.4
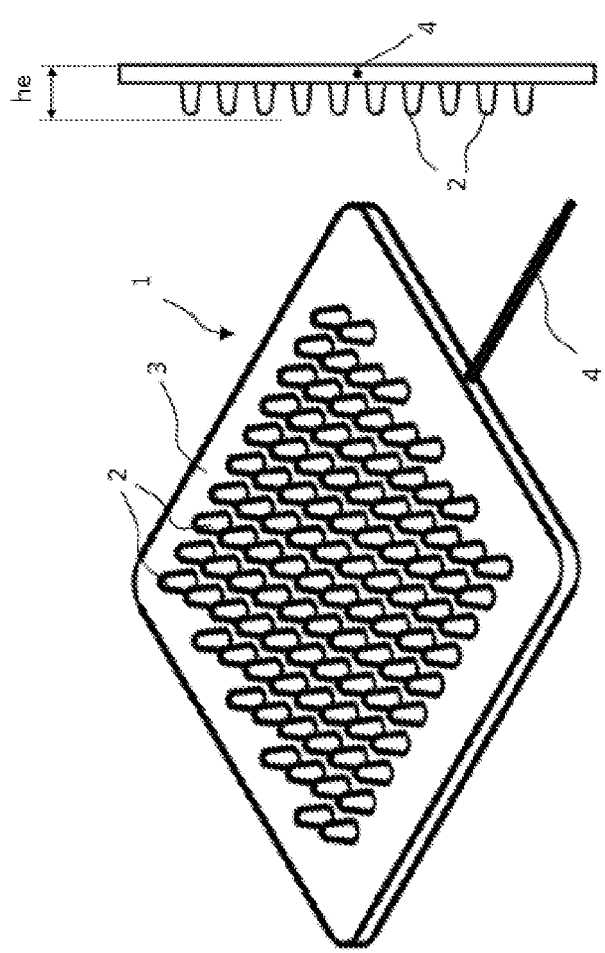
FIG.1

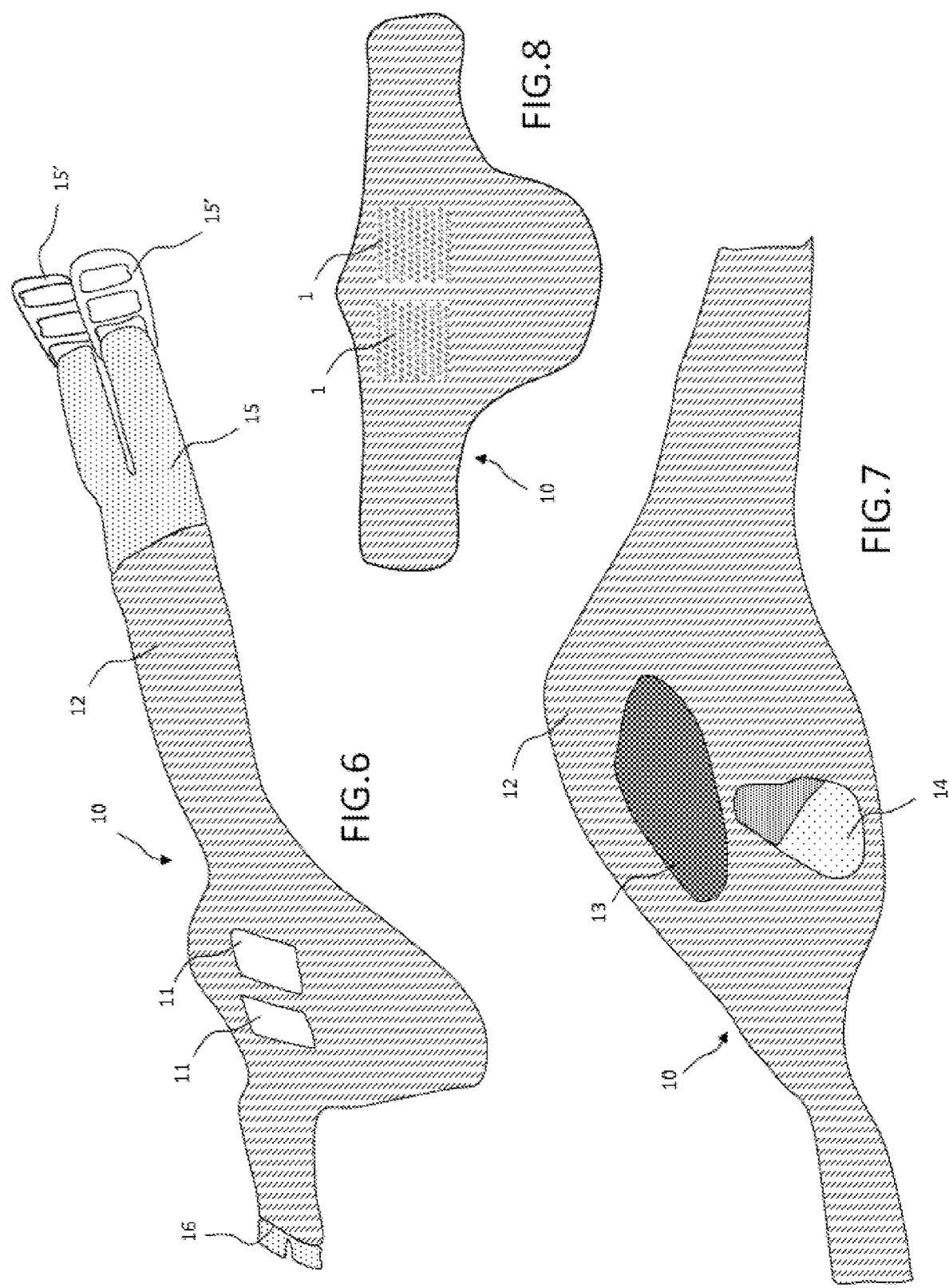

SURFACE ELECTRODE FOR ACQUIRING A CARDIAC ACTIVITY OF A COATED ANIMAL, ELECTRODE SUPPORT, STRAP, ASSOCIATED METHODS

CROSS-REFERENCE TO RELATED APPLICATIONS

This application is the U.S. National Stage of PCT/EP2018/068812, filed Jul. 11, 2018, which in turn claims priority to French patent application number 1700747 filed Jul. 12, 2017. The content of these applications are incorporated herein by reference in their entireties.

FIELD

The field of the invention relates to the field of surface electrodes aiming at recording a cardiac activity of haired animals. More particularly, the field of the invention relates to recording a cardiac activity of a horse, supports aiming at holding one or more electrodes and specific processings of the recorded data.

STATE OF THE ART

At present, in order to measure the cardiac electric activity of an animal, it is recommended to shear a belly or chest part of the animal and to add an electrode gel thereto in order to affix surface electrodes thereto.

For medical purposes, this solution enables a cardiac rhythm to be recorded. However, it is difficult to obtain a cardiac electric activity during exercise since the animal has to keep the electrodes for a time lapse.

Finally, there is a need for correlating the cardiac activity with motions of the horse, and sometimes even during competitions. To date, there are connected saddles enabling a gait of a horse to be deduced, for example from the data analysis relating to its kinematics and/or its dynamics. However, no consideration of the cardiac activity enables kinematics data to be correlated, with cardiac data.

SUMMARY OF THE INVENTION

The aim of the invention is to overcome the abovementioned drawbacks.

According to a first aspect, the invention relates to a surface electrode for recording a cardiac activity of a haired animal, characterized in that it includes a one-piece structure formed of a polymer material in which conductive elements are distributed, said structure including a base and a plurality of projections able to go through a coat.

One advantage is to make it possible to go through the hair of a haired animal.

According to one embodiment, the projections form substantially conical pins or spikes.

According to one embodiment, the polymer material is a silicone and the conductive elements are a graphite powder. One advantage is that this material avoids causing discomfort to the horse.

According to one embodiment, a lead wire is molded in the base and transmits an electric potential resulting from all the potentials measured by each pin.

According to one embodiment, the number of pins is between 25 and 75. Such a number of pins makes it possible to overcome the area deficiency problem related to the hair of a horse for example.

According to another aspect, the invention relates to a set of surface electrodes according to the invention, said set comprising a first reference electrode and a second electrode, said electrodes being electrically insulated from each other and able to measure two electric potentials at the surface of an animal body.

According to another aspect, the support for at least one electrode comprises an electronic module including at least one memory, a calculator and a first electric interface to receive the electric signals acquired by at least one electrode and a second, wireless interface to transmit data to a third party electronic equipment.

According to one embodiment, the support comprises at least one opening designed for passing pins so as to direct them towards the body of an animal when the support is held on the latter, said opening having a smaller area than the area of the base of the electrode so as to hold said electrode.

According to one embodiment, the electronic module further comprises an inertial unit including at least one accelerometer, a gyroscope or a gyrometer and a compass delivering parameters in real time enabling the kinematics of an animal wearing said support to be reconstructed.

According to one embodiment, the support includes an induction charging battery.

According to one embodiment, the support includes a mechanical backing arranged on the external part of the support and protecting an internal location of said support including the electronic module.

According to another aspect, the invention relates to an electrode support comprising a first reference electrode and a second electrode, said electrodes being electrically insulated from each other and able to measure two electric potentials at the surface of a haired animal body, said electrode support further comprising an electronic module including at least one memory, a calculator and a first electric interface to receive the electric signals acquired from each electrode for recording a cardiac activity of said haired animal, at least one electrode including a one-piece structure formed of a polymer material in which conductive elements are distributed, said structure including a base and a plurality of projections able to go through a coat.

According to one embodiment, each electrode includes a one-piece structure formed of a polymer material in which conductive elements are distributed, said structure including a base and a plurality of projections able to go through a coat.

According to one embodiment, the number of projections of each electrode is greater than 14. According to another example, the number of projections is greater than 20. One interest is to obtain a sufficient ratio of the number of projections to the signal quality while avoiding pain for the animal.

According to one embodiment, the electronic module includes a second interface to transmit data to a third party electronic equipment, said second interface being a wireless interface.

According to one embodiment, the electronic module further comprises an inertial unit including at least one accelerometer, a gyroscope or a gyrometer and a compass delivering parameters in real time enabling an instantaneous kinematics of said animal wearing said electrode support to be determined.

The electrode support of the invention can be combined with any described alternatives of electrodes and of integration of different components such as the inertial unit or the electronic module.

According to another aspect, the invention relates to a horse-riding strap including a support according to the invention, said support including a tightening element to be held on the flank or belly of a horse.

Another object of the invention relates to a method for generating an animal gait indicator including:
  recording an electric signal from acquiring at least one surface potential obtained from at least one surface electrode of the invention;
  filtering the electric signals acquired for obtaining a given signal to noise ratio;
  extracting electric parameters from the electric signals filtered including at least one cardiac rhythm;
  comparing the data extracted with data recorded in a memory so as to characterize a gait among a set of possible gait choices.

According to one embodiment, the method comprises:
  determining a gait indicator;
  measuring diagonal half-strides;
  a step of comparing the diagonal half-strides to produce relative gait deviations;
  generating a load distribution on each limb of the horse from a predefined rule associating relative gait deviations with a load compensation.

According to another aspect, the invention relates to a method for generating an indicator relating to the kinematics of an animal including:
  acquiring signals of an inertial unit arranged in an electrode support according to the invention;
  calculating a parameter related to the instantaneous kinematics of the animal comprising:
    calculating a gait indicator among the following gaits: {Gallop, Trot, Walk} of the animal from a function, or;
    calculating a load distribution on each limb of the animal or,
    calculating a characterization of a jump of the animal comprising at least the height of a jump.

One advantage is to use a single support to perform a cardiac measurement and a measurement of the animal's kinematics and motion dynamics. Thus, the electrodes and the unit are held by a single support. The corrections made that can be performed in case of noisy measurements can for example be advantageously used for each measurement performed on the animal.

According to one embodiment, the method further comprises:
  generating a first graphical representation representing the four limbs of said animal and a load value associated with each of said limbs, said values being either updated instantaneous values with a predefined sampling period, or a mean value over a predefined time lapse, and/or;
  generating a second graphical representation representing a curve forming a parabola indicating the height value of the maximum jump and the angle of attack of said jump.

BRIEF DESCRIPTION OF THE DRAWINGS

Further characteristics and advantages of the invention will appear upon reading the following detailed description, with reference to the appended figures, which illustrate:
FIG. 1: a perspective view of an exemplary electrode of the invention;
FIGS. 2, 3, 4: various 2D views of an exemplary electrode of the invention;
FIG. 6: a perspective view of the external face of an exemplary strap of the invention;
FIG. 7: a perspective view of the internal face of an exemplary strap of the invention;
FIG. 8: a front face of an exemplary strap of the invention.

DESCRIPTION

Figure 5:
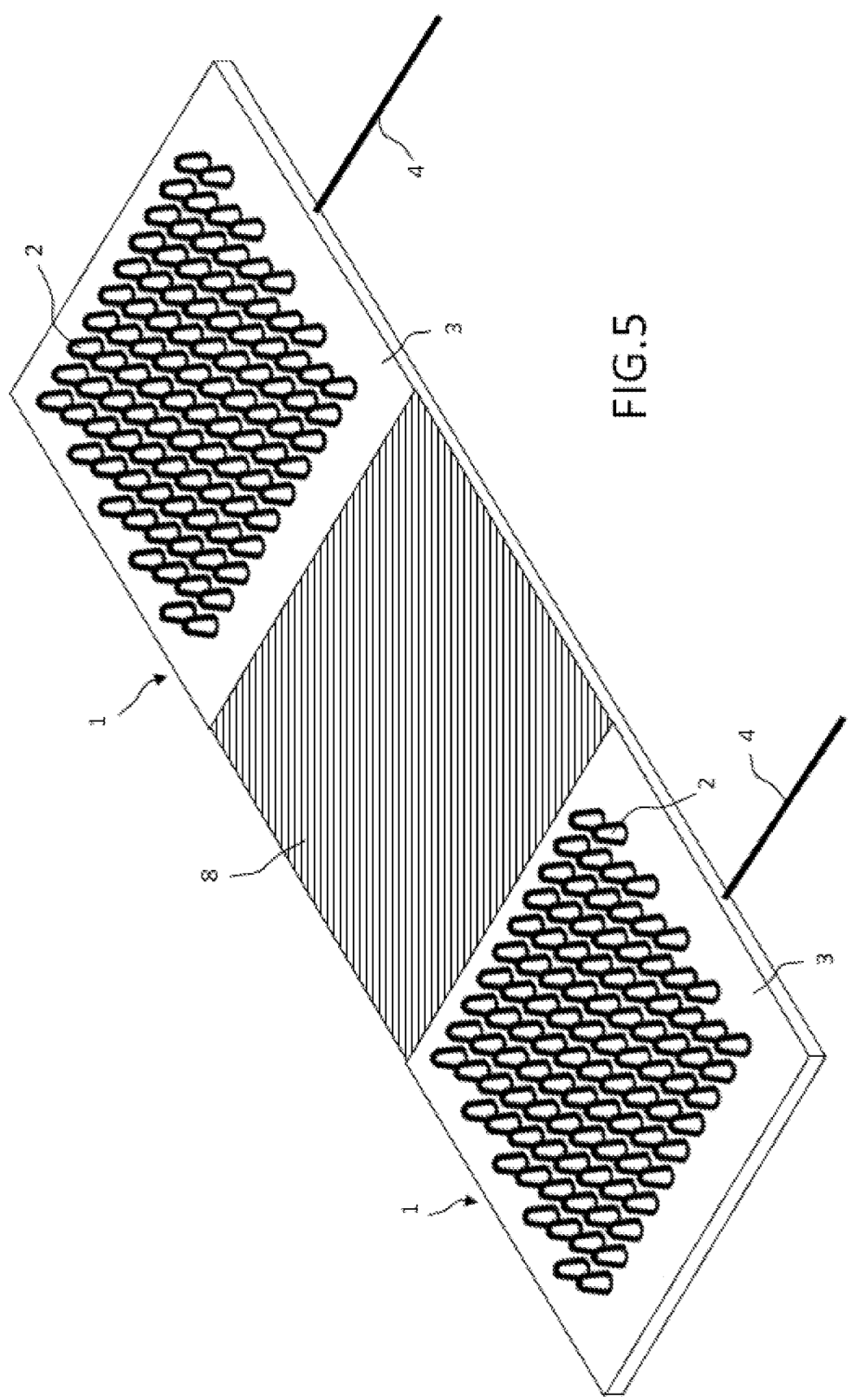
FIG. 5: an exemplary electrode structure including two electrodes of the invention.

FIG. 1 represents a perspective view of an exemplary electrode 1 of the invention. FIGS. 2, 3, 4 represent front, end and side views of the electrode 1 of the invention, respectively.

Functions

According to one embodiment, the electrode 1 includes three functional parts:
  a set of pins 2 for contacting the skin of an animal by passing through a coat;
  a base 3 enabling the pins 2 to be held and a substantially identical load to be exerted on each pin 2 against the surface of an animal skin;
  an electric interface 4, for example as an electric wire or a cable enabling an electric signal acquired by said electrode 1 to be conveyed to an electric interface of an electronic module (not represented).

One advantage of such an electrode is to be easily integrated into a strap, for example for a horse, such as a bib represented in FIGS. 6, 7 and 8. The invention is concerned with the electrode as such and also with a support such as a bib strap or any other strap type such as an anatomical strap, a strap protector or a surcingle.

Material

According to one embodiment, the electrode 1 is made of a polymer material including a conductive element. According to a first alternative, the material is a silicone. According to an example of this first alternative, the material is a silicone elastomer. One advantage of the silicone material is that it has a low resistivity and thus promotes flow of electric charges by means of the conductive elements.

According to one example, the silicone used can be silicone.

According to one second alternative, the material is a plastomer. According to a third alternative, the material is a resin or a gum.

One interest of such an electrode is to limit the load applied to an animal's skin due to the use of a deformable material.

Manufacture

According to one embodiment, the electrode 1 is molded from a mold for manufacturing said electrode 1. According to one embodiment, the electrode 1 is a one-piece electrode, which is manufactured as a single piece.

According to one embodiment, the lead wire 4 is molded in the bulk of the electrode 1 while being manufactured.

According to this embodiment, the electric wire 4 is positioned so that its end is positioned closest to the symmetry of the electrode 1, for example at its center.

According to another embodiment, the electric wire 4 is arranged in the base 3 therethrough for example as represented in dotted lines in FIG. 2 representing the electrode in a front view. It is preferably stripped in the constituent portion of the base 3 of the electrode 1. By way of example, a stripped copper electric cable 4 can be positioned within the conductive silicone base 3. One advantage is to obtain a maximum signal power collected by the electric wire 4 in order to make better use of the electric signals.

According to one embodiment, the conductive element is distributed in the bulk of the electrode 1 as a conducting powder. According to one embodiment, the powder is mixed with the polymer material before curing. According to one exemplary embodiment, the powder is a graphite. Any other conductive powder can be used.

Shape

According to one embodiment, the electrode 1 has a substantially square shape. According to another embodiment, the electrode 1 has a substantially circular shape. These shapes have an interest due to their natural symmetry which guarantees fidelity recording of electric potentials measured at the skin surface.

Any other shape for the electrode 1 with a plurality of available pins 2 can be adapted, namely for example a rectangular shape, an elliptic shape, or any other ergonomic shape adapted to extend along the contour of an animal's belly or the contour of its flank.

According to one embodiment, the electrode 1 includes an area between 40 cm$^2$ and 100 cm$^2$. According to one embodiment, a mean diagonal or a mean diameter includes a characteristic length from 8 to 14 cm.

According to one embodiment, the thickness of the base is between 1 and 6 mm. A thickness from 2.5 mm to 4 mm allows a good compromise to be reached between limiting the electric signal attenuation, electric conductivity, mechanical strength avoiding material tearing, support strong enough to hold the pins. For example, a 3 mm thickness can be chosen.

Distribution of Pins

According to one embodiment, the electrode 1 includes at least two pins 2. According to one embodiment, the electrode 1 includes an even number of pins 2 in order to set a distribution plane having a geometric symmetry that is easy to implement.

According to one embodiment, the electrode 1 of the invention includes between 10 and 100 pins. The number of pins 2 can be determined as a function of the animal's coat type. There are parameters enabling a coat to be characterized, such as hair density, hair length, hair stiffness and/or thickness. The number of pins 2 can also be dimensioned as a function of the animal's size, its weight, the amplitude of the maximum cardiac electric pulse measured at the myocardium surface or at the skin surface, in this case the aim is to set a reference.

According to one embodiment, the number of pins 2 is between 35 and 75, and for example in a range between 50 and 60. The latter two ranges are particularly adapted for measuring the cardiac rhythm of the horse.

According to one embodiment, each electrode includes at least 14 pins. This number of pins enables a possibly usable minimum signal to be obtained. According to another embodiment, each electrode includes at least 20 pins. Such a configuration enables the quality of the acquired signal to be improved.

Dimensioning the Pins

According to one embodiment, the pins 2 have a three dimension geometry including a slight slope so as to form a cone. According to one embodiment, the end of each pin 2 forms a rounded part to avoid causing pain to the animal when the electrode 1 is held integral with the animal, for example from a strap 10.

According to one embodiment, the height of the pins 2 is 5 mm so as to pass between the hair of a dense coat, for example that of a horse. Preferably, the height of pins 2 is between 3 mm and 7 mm. A range defined between 4 mm and 6 mm is particularly interesting in the case of the horse because of the mean hair density of the latter.

According to one embodiment, the pin-to-pin distance is in the order of 3 mm and can be chosen in a wide range between 1 mm and 10 mm. Such a range enables a configuration, in which the pins 2 are in contact with the skin of a horse and the hair spread by the pins 2 is disposed between said pins 2, to be obtained. The configuration thus chosen is particularly adapted to the coat of a horse and enables the displaced volume of hair to be disposed between the pins. One advantage of the electrode 1 of the invention is to be able to adapt to a shaved horse as well as to a long haired horse.

One advantage of using pins is to make it possible to go through the coat of an animal.

Another advantage of the presence of pins 2 is the decrease in noise in the reception spectrum when acquiring the signal the high level of which is especially related to the animal's motions. This frequency noise is particularly significant in the horse. The pins 2 then act as mechanical springs enabling part of the vibrations and chocks disturbing measurements of the cardiac rhythm to be absorbed. Furthermore, they enable the electrode 1 to be held in contact with the animal's skin.

Set of Electrodes

According to one embodiment, the invention relates to a set of at least two electrodes 1. According to this embodiment, both electrodes 1 enable a couple of electrodes to be formed in order to determine the difference between the potentials measured. When two electrodes 1 are used, the difference between electric potentials measured makes it possible to generate a standardized electric signal which is built relative to two recordings. This solution enables part of the noise to be suppressed and the part of the electric signal related to the beat to be processed.

When two electrodes are arranged into a same support, an insulating part is arranged between each electrode so as to prevent charges from passing from a first electrode to the second electrode.

According to one embodiment, both electrodes 1 are manufactured in a same structure. FIG. 5 represents an embodiment of a single support structure {3, 8} including an intermediate insulating support 8 between both conductive supports 3. The part 8 enables both electrodes 1 to be electrically insulated from each other. It ensures that no charge can switch from one electrode 1 to the other. Each support 3 enables electric charges to be conveyed up to the electric wire 4.

One advantage is to have a single product enabling both electrodes 1 to be associated to determine a difference of electric potentials. Such a solution is also simple to place on a horse strap 10.

According to one embodiment, a plurality of electrodes 1 is used so as to perform more accurate measurements of the cardiac rhythm.

According to one embodiment, electric signals are analogically processed. According to one embodiment, an electronic module acquires analog data and includes an analog/digital converter. According to another embodiment, an analog/digital converter processes the signals so as to deliver digital data to the electronic module.

Electronic Module

According to one aspect, the invention relates to a support for one or more electrodes including an electronic module enabling electric signals measured by the electrodes 1 to be used.

The electronic module includes a calculator such as a microprocessor and/or a microcontroller in order to perform operations for processing signals, extracting patterns or calculating averages. Any other operation type for making use of the signals acquired by the accelerometers, gyrometers or compasses can be performed by a dedicated calculator or a calculator shared with that processing data relating to the electric activity recorded.

The electronic module further includes a memory enabling data extracted from the signals to be recorded and data from a collection to be recorded. The latter data enable reference data to be defined in order to perform comparison, correlation and checking operations.

Another memory or the same memory can be used to record signals coming from kinematics and dynamics sensors, which are gyrometers, accelerometers, compasses.

Wireless Interface

According to one embodiment, the electronic module includes a wireless interface enabling data to be transmitted to a remote equipment, such as a tablet computer, PC or Smartphone. By way of example, the wireless interface can be a Bluetooth interface, a RFID interface, a NFC interface or a WIFI interface.

One interest is to be able to transmit data relating to a training, a travel or a race to a third party for analysis purposes.

A third party, such as the horse rider, can then after the race, makes use of data relating to the cardiac rhythm of a horse, performance or the good or bad health of the horse.

According to one operating principle, sensors such as electrodes, gyroscopes or gyrometers, accelerometers, compasses acquire data relating to a horse, the memory makes it possible to record the data, the calculator to process them and the wireless interface makes it possible to transmit data processed or not processed to a third party equipment. The transmission can be performed spontaneously or on demand according to the embodiments of the invention.

Gait

Figure 9:
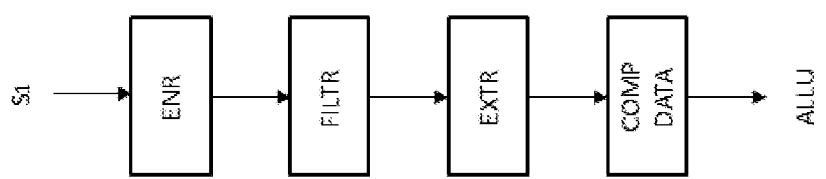
FIG. 9: an embodiment for implementing the method of the invention enabling a gait type of a horse including a strap of the invention to be deduced.

FIG. 9 describes the steps of one embodiment of the method of the invention.

The method of the invention enables an animal gait indicator represented by ALLU in FIG. 9 to be generated. The method includes recording ENR an electric signal S1 from the acquisition of at least one surface potential obtained from at least one surface electrode 1. In the case where two electrodes 1 are utilized, recording ENR a difference of electric potentials is performed. One advantage of the method of the invention is to be able to extract the cardiac rhythm of a horse while the latter is moving and can for example follow a travel. Another advantage is to be able to measure a cardiac activity with an equipment nearly identical to the usually used equipment since the electrode can be advantageously integrated into a strap held against the horse.

The method of the invention includes filtering FILTR the acquired electric signals for obtaining a given signal to noise ratio. Filtering further allows the implementation of a high pass filter to remove the low frequencies as well as the drift in the signal base line.

The signal filtered is preferably in a predefined frequency range which corresponds to the spectral template of a cardiac electric potential of a horse.

Filtering is adapted to select electric signals corresponding to a heart rate between about 20 and 250 beats/min, that is to say [0.3 Hz; 4.2 Hz].

According to one embodiment, filtering enables 50 Hz interference frequency and possibly 60 Hz interference frequency to be eliminated.

The method of the invention comprises a step for extracting EXTR electric parameters from the filtered signals. The first extracted electric parameter is cardiac rhythm.

The method then comprises a step of comparing COMP_DATA the extracted cardiac rhythm with rhythm data pre-recorded in a memory in order to:

either confirm a horse's gait ALLU when the gait has been deduced by another method; this confirmation also enables the electric patterns making false positives to be managed and eliminated;

or directly deduce therefrom a characterization of the horse's gait ALLU.

According to one embodiment, when the electric patterns making false positives, which is corresponding to a characterization error, are recorded, they enable a learning database to be improved.

Kinematics, Dynamics

The method of the invention comprises a step of acquiring a kinematic and dynamic parameter from an accelerometer, a gyrometer and a magnetic compass.

The accelerometer enables accelerations along three axes: ax, ay, az to be measured. The gyrometer enables angular velocities $d\theta$, $d\phi$, $d\alpha$ along three axes to be measured. The magnetic compass, or magnetometer, enables the magnetic field to be measured in micro Tesla.

Processing the accelerometer, gyrometer and magnetometer data enables quaternions which give angular positions $\theta$, $\phi$, $\alpha$ along the three axes and therefore the orientation in space to be deduced therefrom. With $\theta$ being the roll angle, $\phi$ the pitch angle and $\alpha$ the yaw angle.

According to one embodiment, the three functions can be integrated into a same sensor. Data collected by the sensor are called dynamic parameters, there are 9 of them. The method of the invention enables a curve of a horse's jump to be generated from dynamic parameters. This analysis can be performed in addition or alternatively to an analysis of the gait.

A first function F1 gives this curve.

$$F1(ax,ay,az,\theta,\phi,\alpha,d\theta,d\phi,da)=Csaut$$

Figure 12:
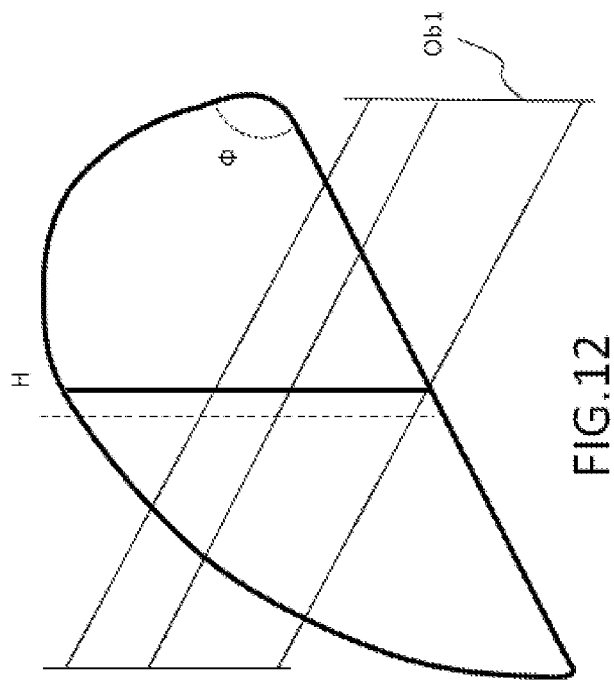
FIG. 12: an exemplary representation of the parabola of a horse jump according to one embodiment of the method of the invention.

According to one embodiment, the method of the invention offers the possibility of displaying the parabola of each jump including the height and jump angle $\phi$ as represented in FIG. 12.

Measurement of Load Distribution

Figure 10:
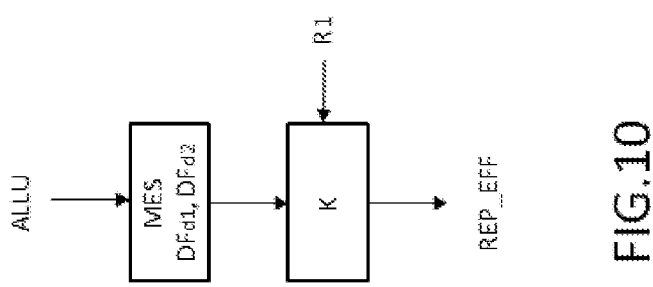
FIG. 10: an embodiment for implementing the method of the invention enabling the load/stress distribution on each of the limbs to be known.

According to one embodiment, the method of the invention comprises detecting the horse's gait, said gait being represented by ALLU in FIG. 10, for example whether it is galloping, trotting or walking.

Different embodiments enable a characterization of the horse's gait to be deduced. According to a first embodiment, this gait can be deduced from measurements performed by the inertial unit including in particular the accelerometer. According to a second embodiment, the gait characterization can be deduced from the analysis of the cardiac rhythm.

According to a third embodiment, both inertial and cardiac measurements can be combined together to consolidate the characterization result.

According to the first embodiment, determining a characteristic gait ALLU is obtained by analyzing the horse's instantaneous velocity. It can be advantageously corroborated with the cardiac rhythm. The analysis of the horse's velocity is determined by the electronic module including accelerometers.

When the gait ALLU is, for example, deduced from the cardiac rhythm previously determined by the steps of the method of FIG. 9, variations in the cardiac rhythm are taken into account in the method of the invention.

According to one embodiment, the method of the invention comprises measuring at least one half-stride at the limbs taken in twos according to each diagonal biped, denoted as diagonal. A first diagonal line is defined by the right front limb and the left rear limb and a second diagonal line is defined by the left front limb and the right rear limb.

These measurements are particularly advantageous to measure the load distribution on the diagonals when the horse is trotting.

This step is denoted as $MES\_DF_{d1}$ and $MES\_DF_{d2}$ in FIG. 10.

For this purpose, a predefined rule $R_1$ can be configured so as to establish a link between half-strides of each of the diagonal lines d1, d2 with a relative load compensation. This purpose of this step denoted as K, is to generate a load or stress distribution plane on each of the horse's limbs.

Figure 11:
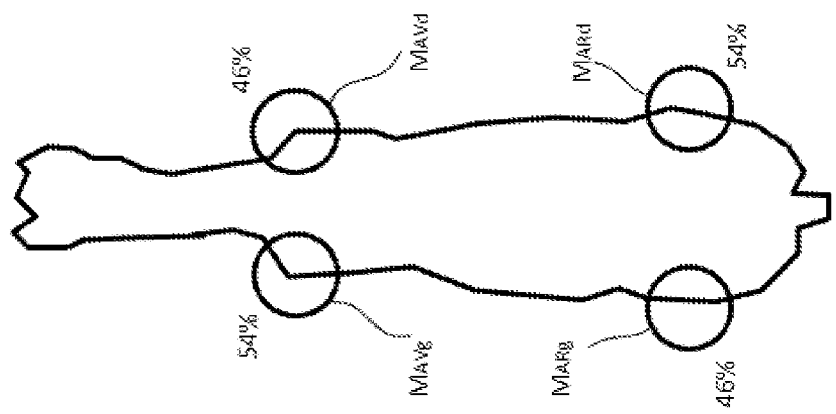
FIG. 11: an exemplary load/stress distribution on each limb of a horse from the execution of an embodiment of the method of the invention.

According to one embodiment, the method for generating a gait indicator comprises acquiring signals from the inertial unit, including the gyroscope, the accelerometer and the compass. According to one embodiment, certain gait parameters are measured for each half-stride of the horse. According to one embodiment, the method comprises generating a graph with the load distribution on each of the limbs as is represented in FIG. 11. A first graph can be generated with the instantaneous load distribution on each limb. According to another example which can be combined with the previous one, a graph including cumulated loads can be generated. This graph makes it possible to observe gait asymmetries over time, bad postures or habits of the horse or also an injury or pain compensated by a load dissymmetry.

According to another embodiment, generating a graph with the angle of attack and height of the jump can be performed from the function $F_1$ previously described. One advantage is to be able to generate a qualitative representation of a jump so that it can be appreciated a posteriori.

The method of the invention enables a load dissymmetry applied on each of the limbs to be deduced as a function of the measured differences in lateral half-strides. The method of the invention makes it possible to generate a representation of the locomotion symmetry deduced from compensatory loads, especially as a percentage on each diagonal. FIG. 11 gives an exemplary representation including a percentage distribution of loads/stresses on each of the limbs: left front $M_{AVg}$, right front $M_{AVd}$, left rear $M_{ARg}$, right rear $M_{ARd}$.

One advantage is to measure a dissymmetry of the horse's loads on the ground especially for different gaits on the ground.

According to different embodiments, the method of the invention makes it possible to calculate the number of obstacles of a travel, the mean and/or maximum height reached by a horse or also an assessment of a difficulty level of the travel.

According to one embodiment, the electrode support 10 comprises a fastener to hold the support in contact with the horse's coat, for example using a tightening means such as a fastened belt. According to one embodiment, the support 10 is for being held against a horse coat so as to display the electrodes and more particularly the electrode pins in contact with the horse's coat.

According to one embodiment, the support 10 comprises an opening for passing the pins 2 which are to be directed facing a coat. According to one embodiment, the support 10 comprises a smaller opening than the dimension of each electrode so as to form an edge enabling the electrode to be held in its support.

The invention claimed is:

1. Horse-riding strap including an electrode support comprising at least one electrode able to measure an electric potential at the surface of a haired animal body, said electrode support further comprising an electronic module including at least one memory, a calculator and a first electric interface to receive electric signals acquired from each electrode for recording a cardiac activity of said haired animal, wherein the at least one electrode includes a one-piece structure formed of a polymer material in which conductive elements are distributed, said structure including a base and a plurality of projections able to go through a coat; wherein the electrode support comprises at least one opening designed for passing the plurality of projections so as to direct them towards the body of a horse when the electrode support is held on the latter, said opening having a smaller area than the area of the base of the at least one electrode so as to hold said at least one electrode.

2. The horse-riding strap according to claim 1, wherein the plurality of projections form substantially conical pins.

3. The horse-riding strap according to claim 1, wherein the polymer material is a silicone and wherein the conductive elements are a graphite powder.

4. The horse-riding strap according to claim 1, wherein a lead wire is molded in the base and transmits an electric potential resulting from all the potentials measured by each projection.

5. The horse-riding strap according to claim 1, wherein the number of the plurality of projections is between 25 and 75.

6. The horse-riding strap according to claim 1, wherein the number of the plurality of projections of each electrode is greater than 14.

7. The horse-riding strap according to claim 1, wherein the electronic module includes a second interface to transmit data to a third party electronic equipment, said second interface being a wireless interface.

8. The horse-riding strap according to claim 7, further comprising a mechanical backing on the external part of the electrode support and protecting an internal location of said electrode support including the electronic module.

9. The horse-riding strap including a support according to claim 7, further comprising a tightening element to be held on the flank or belly of a horse.

10. The horse-riding strap according to claim 1, wherein the electronic module further comprises an inertial unit including at least one accelerometer, one gyroscope or one gyrometer and one compass delivering parameters in real time enabling instantaneous kinematics of said horse carrying said horse-riding strap to be determined.

11. The horse-riding strap according to claim 1, further comprising an induction charging battery.

12. A method for generating an indicator relating to the kinematics of an animal, the method comprising:
acquiring signals of an inertial unit arranged in a horse-riding strap according to claim 10;

calculating a parameter related to instantaneous kinematics of the animal comprising:
  calculating a gait indicator among the following gaits: {Gallop, Trot, Walk} of the horse from a function, or;
  calculating a distribution of loads on each limb of the horse or,
  calculating a characterization of a jump of the horse comprising at least the height of a jump.

13. The method according to claim 12, further comprising:
  generating a first graphical representation representing the four limbs of said horse and a load value associated with each of said limbs, said values being either updated instantaneous values with a predefined sampling period, or a mean value over a predefined time lapse, and/or;
  generating a second graphical representation representing a curve forming a parabola indicating the value of the height of the maximum jump and the angle of attack of said jump.

* * * * *